US009693743B2

(12) United States Patent
Arakita et al.

(10) Patent No.: US 9,693,743 B2
(45) Date of Patent: Jul. 4, 2017

(54) PHOTON COUNTING CT APPARATUS

(71) Applicant: Toshiba Medical Systems Corporation, Otawara-shi (JP)

(72) Inventors: Kazumasa Arakita, Nasushiobara (JP); Masahiro Ozaki, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/722,689

(22) Filed: May 27, 2015

(65) Prior Publication Data

US 2015/0346354 A1 Dec. 3, 2015

(30) Foreign Application Priority Data

May 28, 2014 (JP) ................. 2014-110397

(51) Int. Cl.
| | | |
|---|---|---|
| *G01T 1/16* | (2006.01) |
| *G01T 1/172* | (2006.01) |
| *A61B 6/00* | (2006.01) |
| *G01N 23/04* | (2006.01) |
| *G06T 11/00* | (2006.01) |
| *A61B 6/03* | (2006.01) |
| *G01T 1/20* | (2006.01) |
| *G01T 1/36* | (2006.01) |

(52) U.S. Cl.
CPC ............ *A61B 6/4241* (2013.01); *A61B 6/032* (2013.01); *G01N 23/046* (2013.01); *G01T 1/1606* (2013.01); *G01T 1/172* (2013.01); *G01T 1/2018* (2013.01); *G01T 1/36* (2013.01); *G06T 11/005* (2013.01); *G01N 2223/50* (2013.01)

(58) Field of Classification Search
None
See application file for complete search history.

(56) References Cited

U.S. PATENT DOCUMENTS

| 9,155,516 B2* | 10/2015 | Wang ................... A61B 6/4241 |
| 2002/0109091 A1* | 8/2002 | Overdick ............. G01N 23/046 |
| | | 250/336.1 |
| 2009/0008564 A1* | 1/2009 | Balan .................... G01T 1/1644 |
| | | 250/366 |
| 2010/0193700 A1* | 8/2010 | Herrmann ............... G01T 1/171 |
| | | 250/395 |
| 2012/0300896 A1* | 11/2012 | Flohr .................... A61B 6/032 |
| | | 378/5 |

(Continued)

FOREIGN PATENT DOCUMENTS

JP 2013-000227 1/2013

*Primary Examiner* — Michael Logie
(74) *Attorney, Agent, or Firm* — Oblon, McClelland, Maier & Neustadt, L.L.P.

(57) ABSTRACT

According to on embodiment, a photon counting CT apparatus includes a hybrid detector and processing circuitry. The hybrid detector includes CT detectors and PCCT detectors. The CT detectors output integral signals concerning the detected X-rays. The PCCT detectors output a count signal for each of a plurality of energy bands concerning the detected X-rays. The processing circuitry estimate a count signal concerning an estimation target CT detector of the CT detectors based on an integral signal output from the estimation target CT detector and a count signal output from the PCCT detector. And the processing circuitry reconstruct an image based on the estimated count signal and the count signal.

13 Claims, 10 Drawing Sheets

(56) References Cited

U.S. PATENT DOCUMENTS

| | | | | |
|---|---|---|---|---|
| 2013/0010921 A1* | 1/2013 | Sagoh | ................... | A61B 6/032 378/19 |
| 2014/0328465 A1* | 11/2014 | Herrmann | ................. | G01T 1/17 378/62 |
| 2015/0223766 A1* | 8/2015 | Besson | ................ | G01T 1/2985 378/5 |

* cited by examiner

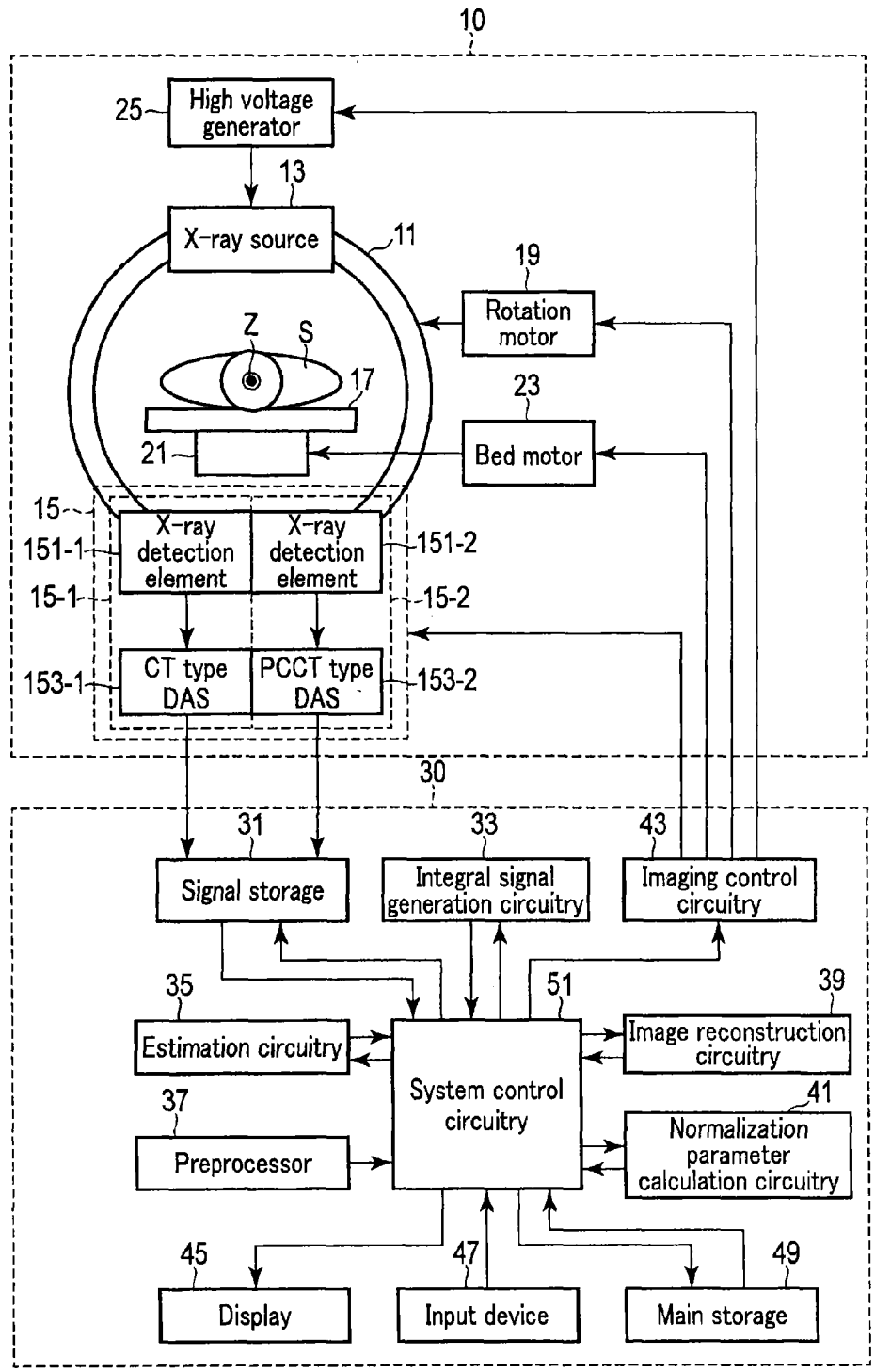
F I G. 1

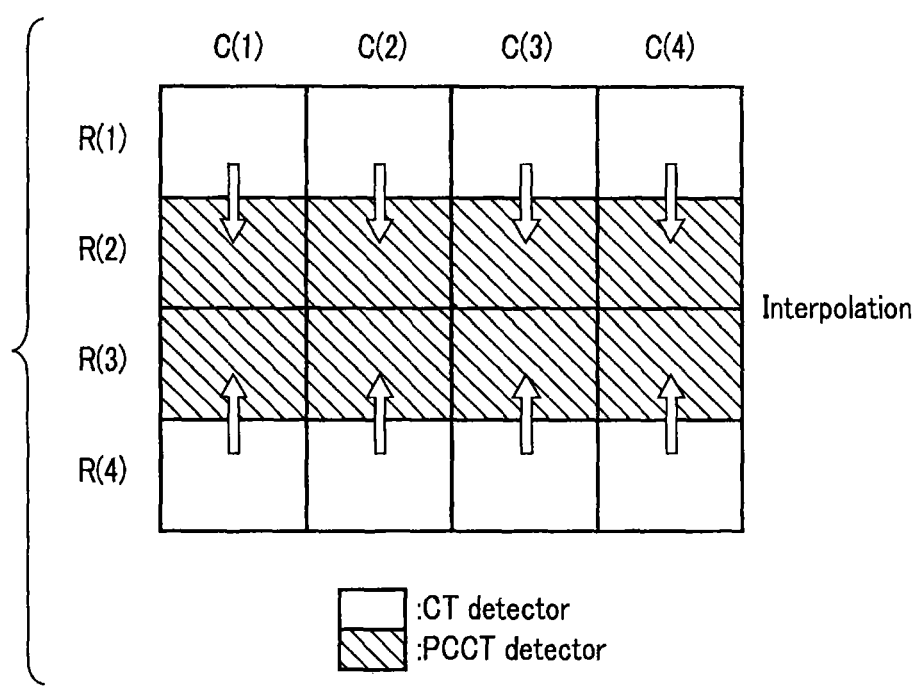
F I G. 12

PHOTON COUNTING CT APPARATUS

CROSS-REFERENCE TO RELATED APPLICATIONS

This application is based upon and claims the benefit of priority from the prior Japanese Patent Application No. 2014-110397, filed May 28, 2014 the entire contents of which are incorporated herein by reference.

FIELD

Embodiments described herein relate generally to a photon counting CT apparatus.

BACKGROUND

In order to implement photon counting type CT (Computed Tomography), a detector including a signal processing circuit (DAS: Data Acquisition System) capable of performing energy discrimination and optimal X-ray detection elements is required. For this reason, a photon counting type CT is higher in manufacturing cost and management cost than an integral type CT. In addition, the integral type CT acquires a signal corresponding to the energy integration of X-ray photons for each view, whereas the photon counting type CT acquires a signal corresponding to the count value of X-ray photons for each energy band concerning each view. Therefore, the amount of data of signals acquired by the photon counting type CT is larger than that acquired by the integral type CT by the energy resolution. A solution to the above technical problem is indispensable to the commercial success of the photon counting type CT.

BRIEF DESCRIPTION OF THE DRAWING

FIG. 1 is a block diagram showing the arrangement of a photon counting CT apparatus according to an embodiment;

FIG. 12 is a view showing a concept of interpolation in the array pattern in FIG. 4.

DETAILED DESCRIPTION

Figure 2:
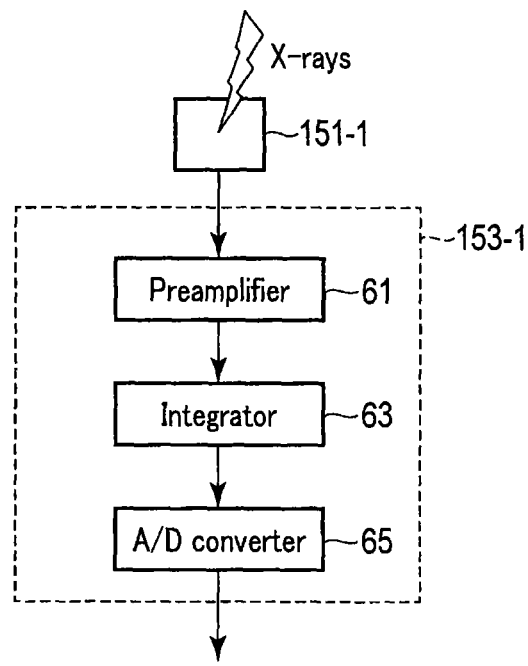
FIG. 2 is a block diagram showing the arrangement of a CT detector in FIG. 1.

In general, according to one embodiment, a photon counting CT apparatus includes an X-ray source, a hybrid detector, and processing circuitry. The X-ray source generates X-rays. The hybrid detector includes a plurality of integral type detectors and a plurality of photon counting type detectors, which detect X-rays generated from the X-ray source. The plurality of integral type detectors output integral signals concerning the detected X-rays. The plurality of photon counting type detectors output a count signal for each of a plurality of energy bands concerning the detected X-rays. The processing circuitry estimate an count signal concerning an estimation target integral type detector of the plurality of integral type detectors based on an integral signal output from the estimation target integral type detector and a count signal output from the photon counting type detector. And the processing circuitry reconstruct an image based on the estimated count signal and the count signal.

The photon counting CT apparatus according to this embodiment will be described below with reference to the accompanying drawing.

FIG. 1 is a block diagram showing the arrangement of the photon counting CT apparatus according to this embodiment. As shown in FIG. 1, the photon counting CT apparatus according to the embodiment includes a gantry 10 and a console 30. The gantry 10 supports a rotating frame 11 having a cylindrical shape so as to allow it to rotate about a rotation axis Z. An X-ray source 13 and a hybrid detector 15 are attached to the rotating frame 11 so as to face each other through the rotation axis Z. An FOV (Field Of View) is set in the bore of the rotating frame 11. A top 17 is inserted into the bore of the rotating frame 11. A rotation motor 19 generates motive power for rotating the rotating frame 11 under the control of an imaging control circuitry 43. The rotating frame 11 rotates about the rotation axis Z at a constant angular velocity upon receiving motive power from the rotation motor 19. For example, an subject S is placed on the top 17. The top 17 is movably supported by a top support mechanism 21. The top support mechanism 21 moves the top 17 upon receiving motive power from a bed motor 23. The bed motor 23 generates motive power for moving the top 17 under the control of the imaging control circuitry 43 in a console 30. The top 17 is positioned such that an imaging region of the subject S is included in the FOV.

The X-ray source 13 is connected to a high voltage generator 25. The high voltage generator 25 applies a high voltage to the X-ray source 13 and supplies a filament current to the X-ray source 13 under the control of the imaging control circuitry 43.

The hybrid detector 15 detects the X-rays generated from the X-ray source 13. The hybrid detector 15 includes a plurality of CT detectors 15-1 and a plurality of PCCT (Photon Counting Computed Tomography) detectors 15-2. The CT detectors 15-1 are detectors for integral type CT. The PCCT detectors 15-2 are detectors for photon counting type CT. The plurality of CT detectors 15-1 and the plurality of PCCT detectors 15-2 are two-dimensionally arrayed on a common detector array surface. One CT detector 15-1 and one PCCT detector 15-2 each form one channel.

Each CT detector 15-1 detects X-rays from the X-ray source 13 and outputs an integral signal concerning the detected X-rays for each view. An integral signal corresponds to the integral value (total value) of the energies of the plurality of X-ray photons detected for each view. More specifically, each CT detector 15-1 includes an X-ray detection element 151-1 and a CT type DAS 153-1, as shown in FIG. 2. The X-ray detection element 151-1 detects X-rays from the X-ray source 13 and outputs a charge pulse (electrical signal) having a peak value corresponding to the energy of a detected X-ray photon. Each charge pulse is supplied to the CT type DAS 153-1. The CT type DAS 153-1 generates an integral signal for each view based on the supplied charge pulses. More specifically, the CT type DAS 153-1 includes a preamplifier 61, an integrator 63, and an A/D converter 65. The preamplifier 61 amplifies the charge pulse output from the X-ray detection element 151-1. The integrator 63 integrates (adds) the charge pulses output from the preamplifier 61 over a period corresponding to one view. Each integrated charge pulse will be referred to as an integral signal. The A/D converter 65 converts an analog integral signal into a digital integral signal. Each integral signal is transmitted to the console 30.

Figure 3:
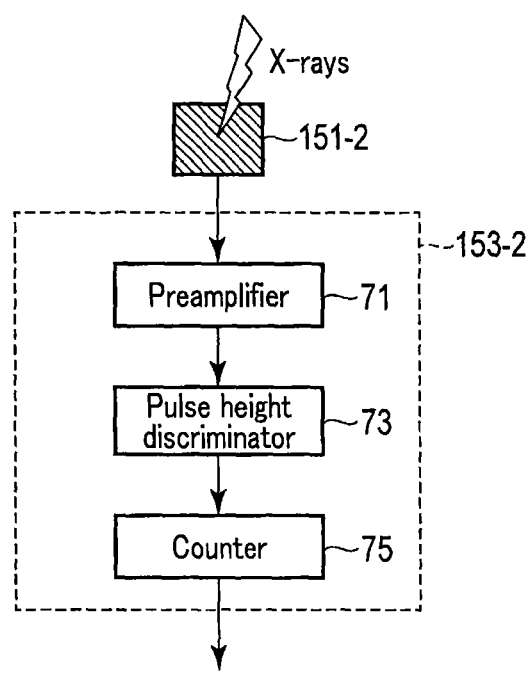
FIG. 3 is a block diagram showing the arrangement of a PCCT detector in FIG. 1.

Each PCCT detector 15-2 detects X-rays from the X-ray source 13 on a photon basis, and outputs count signals concerning detected X-rays concerning a plurality of energy bands included in the energy spectrum of X-rays output from the X-ray source 13 for each view. Each count signal corresponds to the number of X-ray photons detected for each view. More specifically, as shown in FIG. 3, each PCCT detector 15-2 includes an X-ray detection element 151-2 and a PCCT type DAS 153-2. The X-ray detection element 151-2 detects an X-ray photon from the X-ray source 13, and outputs a charge pulse (electrical signal) having a peak value corresponding to the energy of the detected X-ray photon. More specifically, as the X-ray detection element 151-2, a photoelectric conversion element including a scintillator and a photosensor is used. The scintillator generates scintillation photons upon receiving an incident X-ray photon. The number of scintillation photons depends on the energy of the incident X-ray photon. As a photosensor, a SiPM (Silicon PhotoMultiplier) is used. The SiPM includes photomultiplier devices having high sensitivity and high responsiveness which are two-dimensionally arrayed on a silicon by a MEMS (Micro Electro Mechanical System) technique. Each photosensor outputs a charge pulse having a peak value or charge amount corresponding to the energy of an incident X-ray photon. Note that the photosensor according to this embodiment is not limited to a SiPM, and any sensor capable of outputting a peak value corresponding to the energy of an incident X-ray photon can be used. In addition, the photoelectric conversion element according to this embodiment is not limited to an indirect conversion type element including a scintillator and a photosensor, and a direct conversion type element which directly converts an X-ray photon into a charge pulse may be used. The PCCT type DAS 153-2 generates a count signal based on supplied charge pulses. More specifically, the PCCT type DAS 153-2 includes a preamplifier 71, a pulse height discriminator 73, and a counter 75. The preamplifier 71 amplifies the charge pulse output from the X-ray detection element 151-2. Based on the peak value of the charge pulse output from the preamplifier 71, the pulse height discriminator 73 discriminates an energy band to which the charge pulse belongs from a plurality of energy bands. The pulse height discriminator 73 outputs an electrical signal (to be referred to as a discrimination signal hereinafter) having a peak value corresponding to each energy band. The counter 75 counts discrimination signals from the pulse height discriminator 73 concerning each of a plurality of energy bands for each view, and generates a digital count signal representing the count value of X-ray photons detected by the X-ray detection element 151-1.

Note that the X-ray detection element 151-1 and the X-ray detection element 151-2 may be made of the same material and have the same arrangement or may be made of different materials and have different arrangements. When the X-ray detection element 151-1 and the X-ray detection element 151-2 are made of the same material and have the same arrangement, the CT type DAS 153-1 or the PCCT type DAS 153-2 is connected to each of the X-ray detection elements.

The console 30 includes a signal storage 31, an integral signal generation circuitry 33, an estimation circuitry 35, a preprocessor 37, an image reconstruction circuitry 39, a normalization parameter calculation circuitry 41, the imaging control circuitry 43, a display 45, an input device 47, a main storage 49, and a system control circuitry 51.

The signal storage 31 includes a storage unit such as an HDD (Hard Disk Drive), SSD (Solid State Drive), or integrated circuit storage unit. The signal storage 31 is a storage unit which stores a digital signal (data) from the hybrid detector 15. More specifically, the signal storage 31 stores integral signals concerning a plurality of views. Each integral signal is stored in association with the detector address of the CT detectors 15-1 as an output source and a view number. In addition, the signal storage 31 stores count signals concerning a plurality of views concerning each of a plurality of energy bands. A count signal is stored in association with the detector address of the PCCT detectors 15-2 as an output source, a view number, and an energy band number. A detector address is defined by, for example, a combination of a channel number and a row number of the CT detectors 15-1 or the PCCT detectors 15-2.

The integral signal generation circuitry 33 includes predetermined processing circuitry and a predetermined storage unit. The integral signal generation circuitry 33 generates an integral signal based on count signals concerning a plurality of energy bands for each of a plurality of views. More specifically, the integral signal generation circuitry 33 generates an integral signal by integrating count signals concerning energies throughout an X-ray spectrum for each of a plurality of views. The generated integral signal indicates the same physical amount as that of the integral signal output from the CT detectors 15-1.

The estimation circuitry 35 includes predetermined processing circuitry and a predetermined storage unit. When the reconstruction of an integral type image is instructed, the estimation circuitry 35 estimates an integral signal concerning the estimation target PCCT detector 15-2 of the plurality of PCCT detectors 15-2 based on a normalization parameter (to be described later) and the measured count signal output from the estimation target PCCT detector 15-2. The estimation target PCCT detector 15-2 is the PCCT detector 15-2 arranged at a detector address at which an integral signal is missing. When the reconstruction of a photon counting type image is instructed, the estimation circuitry 35 estimates a count signal concerning the estimation target CT detector 15-1 of the plurality of CT detectors 15-1 based on the measured integral signal output from the estimation target CT detector 15-1 and the measured count signal output from the PCCT detector 15-2 spatially close to the estimation target CT detector 15-1. The estimation target CT detector 15-1 is the CT detector 15-1 arranged at a detector address at which a count signal is missing.

The preprocessor 37 includes a predetermined processing circuitry and a predetermined storage unit. When the reconstruction of an integral type image is instructed, the preprocessor 37 generates raw data concerning a plurality of views by preprocessing an integral signal for each of the plurality of views. Raw data based on an integral signal will be referred to as CT raw data hereinafter. When the reconstruction of a photon counting type image is instructed, the preprocessor 37 generates raw data by preprocessing a count signal concerning a plurality of energy bands for each of a plurality of views. Raw data based on a count signal will be referred to as PCCT raw data hereinafter. Preprocessing includes, for example, log conversion, beam hardening correction, and offset correction.

The image reconstruction circuitry 39 includes, as hardware resources, a processing circuitry (processor) such as a CPU (Central Processing Circuitry), MPU (Micro Processing Circuitry), or GPU (Graphics Processing Circuitry) and storage units (memories) such as a ROM (Read Only Memory) and RAM (Random Access Memory). The image reconstruction circuitry 39 reconstructs an image concerning an object based on CT raw data. An image based on CT raw data will be referred to as a CT image hereinafter. The image reconstruction circuitry 39 also reconstructs an image concerning a visualization target energy band of a plurality of energy bands based on PCCT raw data. An image based on PCCT raw data will be referred to as a PCCT image hereinafter. A visualization target energy band may be designated by, for example, the operator via the input device 47 or automatically. As an image reconstruction algorithm, there may be used an existing image reconstruction algorithm such as an analytical image reconstruction method based on an FBP (Filtered Back Projection) method, CBP (Convolution Back Projection) method, or the like or a statistical image reconstruction method based on an ML-EM (Maximum Likelihood Expectation Maximization) method, OS-EM (Ordered Subset Expectation Maximization) method, or the like.

The normalization parameter calculation circuitry 41 includes a predetermined processing circuitry and a predetermined storage unit. The normalization parameter calculation circuitry 41 calculates a normalization parameter used by the estimation circuitry 35. The normalization parameter calculation circuitry 41 calculates normalization parameters based on the integral signals output from the CT detectors 15-1 and the count signals output from the PCCT detectors 15-2. Normalization parameters are respectively calculated for each CT detector 15-1 and each PCCT detector 15-2.

The integral signal generation circuitry 33, the estimation circuitry 35, the preprocessor 37, and the normalization parameter calculation circuitry 41 may be implemented on different circuits or integrated into several circuits. Alternatively, the integral signal generation circuitry 33, the estimation circuitry 35, the preprocessor 37, and the normalization parameter calculation circuitry 41 may be implemented on the image reconstruction circuitry 39.

The imaging control circuitry 43 comprehensively controls the respective types of devices mounted on the gantry 10. The top support mechanism 21 includes, as hardware resources, a processing circuitry (processor) such as a CPU (Central Processing Circuitry) or MPU (Micro Processing Circuitry) and storage units (memories) such as a ROM (Read Only Memory) and RAM (Random Access Memory). More specifically, the imaging control circuitry 43 controls the hybrid detector 15, the rotation motor 19, the bed motor 23, and the generation circuitry 25. More specifically, the rotation motor 19 rotates the rotating frame 11 at a constant angular velocity under the control of the imaging control circuitry 43. The bed motor 23 drives the top support mechanism 21 to slide the top 17 under the control of the imaging control circuitry 43. The high voltage generator 25 applies a high voltage corresponding to a set tube voltage value to the X-ray source 13 and supplies a filament current to the X-ray source 13 under the control of the imaging control circuitry 43. The hybrid detector 15 acquires integral signals and count signals for each view in synchronism with the irradiation timing of X-rays from the X-ray source 13 under the control of the imaging control circuitry 43.

The display 45 displays various kinds of information such as CT images and PCCT images on a display device. As a display device, it is possible to use, for example, a CRT display, liquid crystal display, organic EL display, or plasma display, as needed.

The input device 47 accepts various types of commands and information inputs from the user via an input device. As an input device, it is possible to use a keyboard, a mouse, various types of switches, and the like.

The main storage 49 is a storage unit such as an HDD, SSD, or integrated circuit storage unit which stores various kinds of information. For example, the main storage 49 stores an imaging program, normalization parameters, and the like according to this embodiment.

The system control circuitry 51 includes, as hardware resources, a processing circuitry such as a CPU or MPU and storage units (memories) such as a ROM and RAM. The system control circuitry 51 functions as the main circuitry of the photon counting CT apparatus according to this embodiment. The system control circuitry 51 reads out the imaging program according to the embodiment from the main storage 49, and controls the respective constituent elements in accordance with the imaging program. This makes it possible to perform parallel simultaneous acquisition of integral signals and count signals using the hybrid detector 15.

The array patterns of the CT detectors 15-1 and the PCCT detectors 15-2 according to this embodiment will be described next with reference to FIGS. 4, 5, 6, 7, and 8.

As shown in FIGS. 4, 5, 6, 7, and 8, the plurality of CT detectors 15-1 and the plurality of PCCT detectors 15-2 are two-dimensionally tiled on the detector array surface of the hybrid detector 15. A direction along a rotation axis Z on the detector array surface of the hybrid detector 15 is called a row direction, and a direction perpendicular to the rotation axis Z in the detector array surface is called a channel direction. Referring to FIGS. 4, 5, 6, 7, and 8, assume that the row numbers range from 1 to m, and the channel numbers range from 1 to n. The respective detectors 15-1 and 15-2 are arranged such that the X-ray incident surface of each X-ray detection element is located on the surface of the hybrid detector 15. The CT detectors 15-1 arrayed on the detector array surface are higher in count rate and detection efficiency than the PCCT detectors 15-2, and hence are preferably arrayed in a larger number than the PCCT detectors 15-2. Note that the number of CT detectors 15-1 may be equal to that of PCCT detectors 15-2. In the following description, a bundle of the detectors 15-1 and 15-2 belonging to the same row number will be referred to as a detector row, and a bundle of the detectors 15-1 and 15-2 belonging to the same channel number will be referred to as a detector column.

Figure 4:
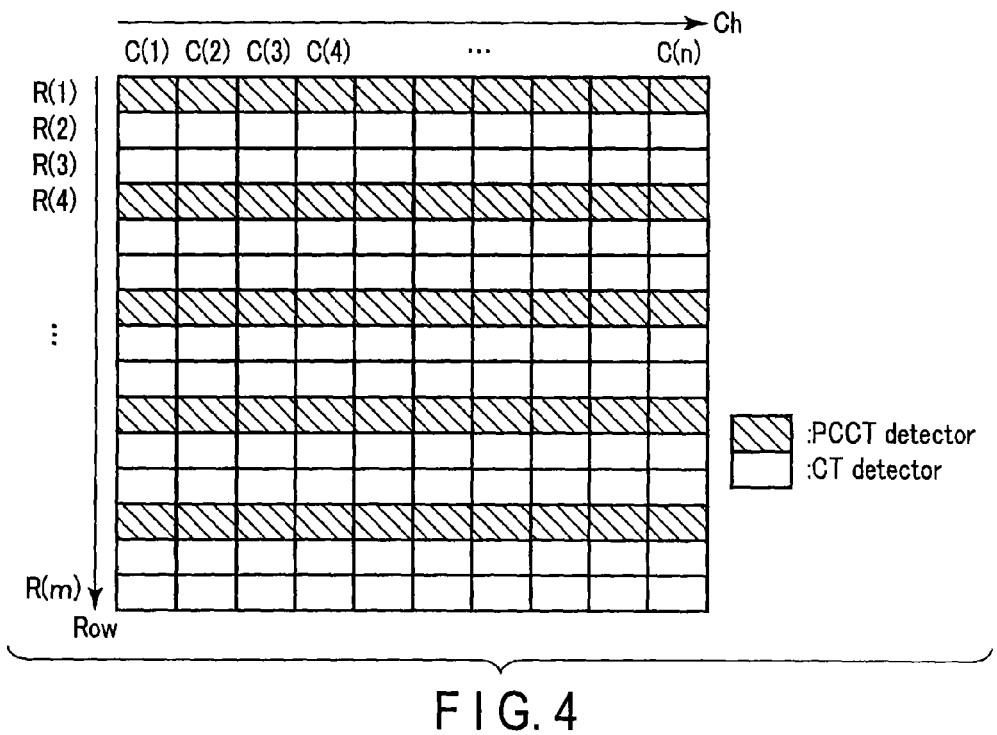
FIG. 4 is a view showing an example of the array pattern of CT detectors and PCCT detectors in FIG. 1.

In the case of the array pattern shown in FIG. 4, the plurality of CT detectors 15-1 and the plurality of PCCT detectors 15-2 are arrayed in the row direction on a detector row basis in a predetermined order. Referring to FIG. 4, detectors of the same type (i.e., the CT detectors 15-1 or the PCCT detectors 15-2) are arranged at all the channel numbers belonging to the same row number. PCCT detector rows are arrayed every predetermined number of rows, and CT detector rows are arranged between the PCCT detector rows. Referring to FIG. 4, the PCCT detector rows are arrayed every two CT detector rows. In this case, the PCCT detectors 15-2 are arranged at all channel numbers C(1) to C(n) belonging to a row number R(1), the CT detectors 15-1 are arranged at all the channel numbers C(1) to C(n) belonging to a row number R(2), and the CT detectors 15-1 are arranged at all the channel numbers C(1) to C(n) belonging to a row number R(3). Note that PCCT detector rows may be arranged every arbitrary number of rows equal to or more than one. In the case of the array pattern in FIG. 4, since all the detectors 15-1 or 15-2 on the same row are of the same type, all the signals required to reconstruct a one-slice image can be acquired by the detectors 15-1 or 15-2 of the same type. This allows even the hybrid detector 15 equipped with the CT detectors 15-1 and the PCCT detectors 15-2 to keep image quality good on a slice basis. In addition, since the CT detectors 15-1 or the PCCT detectors 15-2 of the same type are arrayed throughout one or a plurality of detector rows, structurally independent units can be formed on the detector row basis. It is therefore possible to perform replacement and maintenance on a unit basis.

Figure 5:
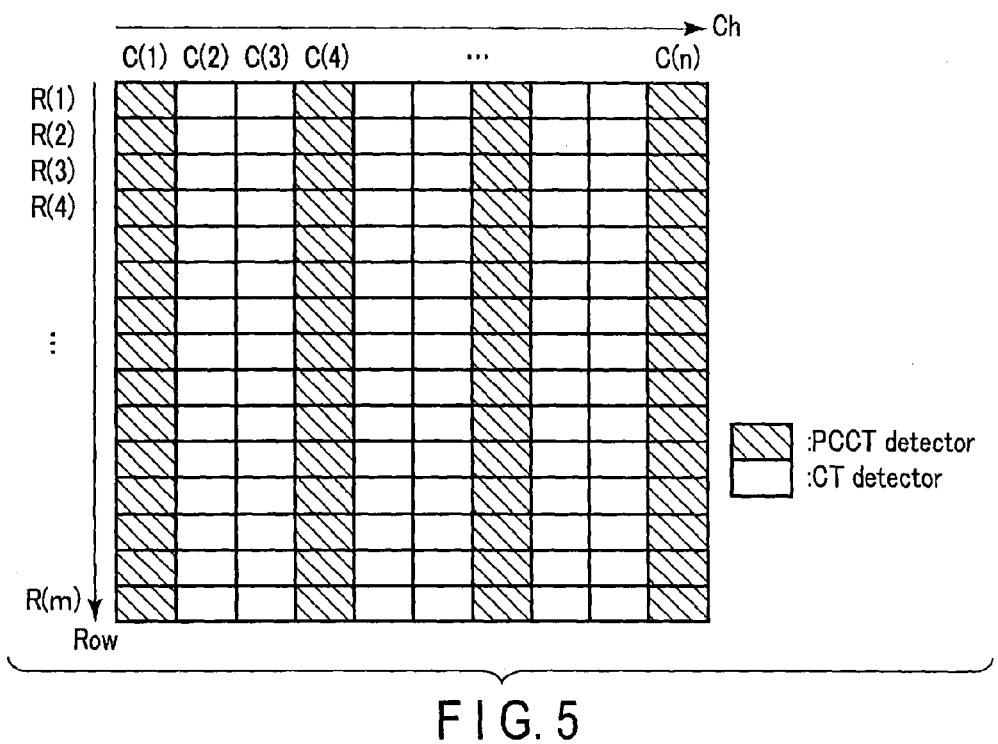
FIG. 5 is a view showing another array pattern of the CT detectors and the PCCT detectors in FIG. 1.

In the case of the array pattern shown in FIG. 5, the plurality of CT detectors 15-1 and the plurality of PCCT detectors 15-2 are arrayed in the channel direction on a detector column basis in a predetermined order. Referring to FIG. 5, the detectors 15-1 or 15-2 of the same type are arranged at all the row numbers belonging to the same channel number. The PCCT detector rows are arrayed every predetermined number of channels, and the CT detector rows are arranged between the PCCT detector rows. For example, the PCCT detectors 15-2 are arranged at all the row numbers R(1) to R(m) belonging to the channel number C(1), the CT detectors 15-1 are arranged at all the row numbers R(1) to R(m) belonging to the channel number C(2), and the CT detectors 15-1 are arranged at all the row numbers R(1) to R(m) belonging to the channel number C(3). Note that PCCT detector rows may be arranged every arbitrary number of rows equal to or more than one. In addition, since detectors of the same type are arrayed throughout one or a plurality of detector columns, structurally independent units can be formed on the detector column basis. It is therefore possible to perform replacement and maintenance on a unit basis.

Figure 6:
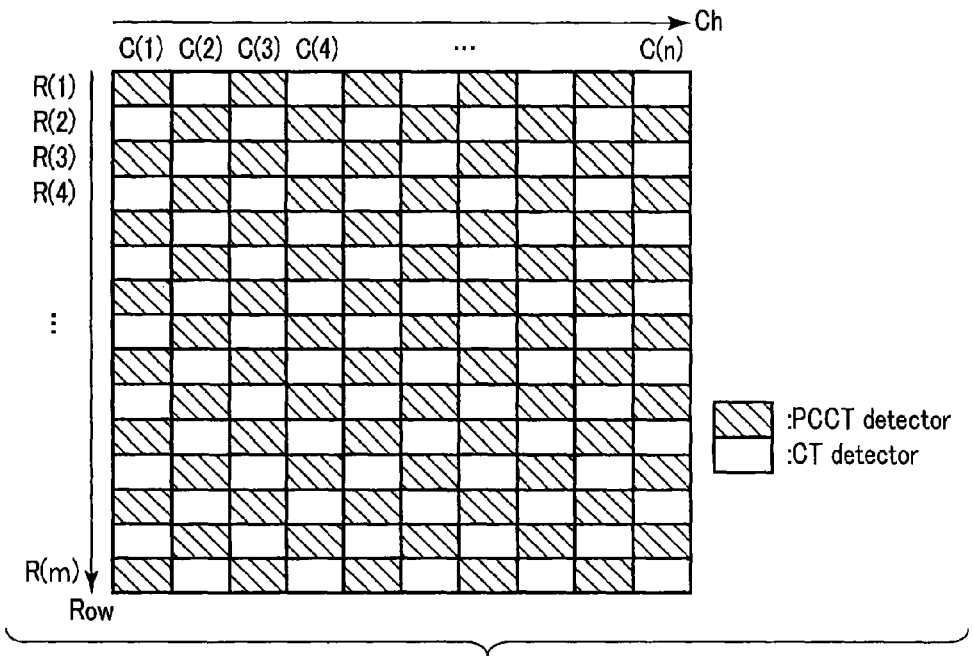
FIG. 6 is a view showing still another array pattern of the CT detectors and the PCCT detectors in FIG. 1.

In the case of the array pattern shown in FIG. 6, the plurality of CT detectors 15-1 and the plurality of PCCT detectors 15-2 are arranged in a checkered pattern. That is, the CT detectors 15-1 and the PCCT detectors 15-2 are alternately arrayed in the row and channel directions. This array pattern makes it possible to acquire measured integral signals and count signals on all the slices.

Figure 7:
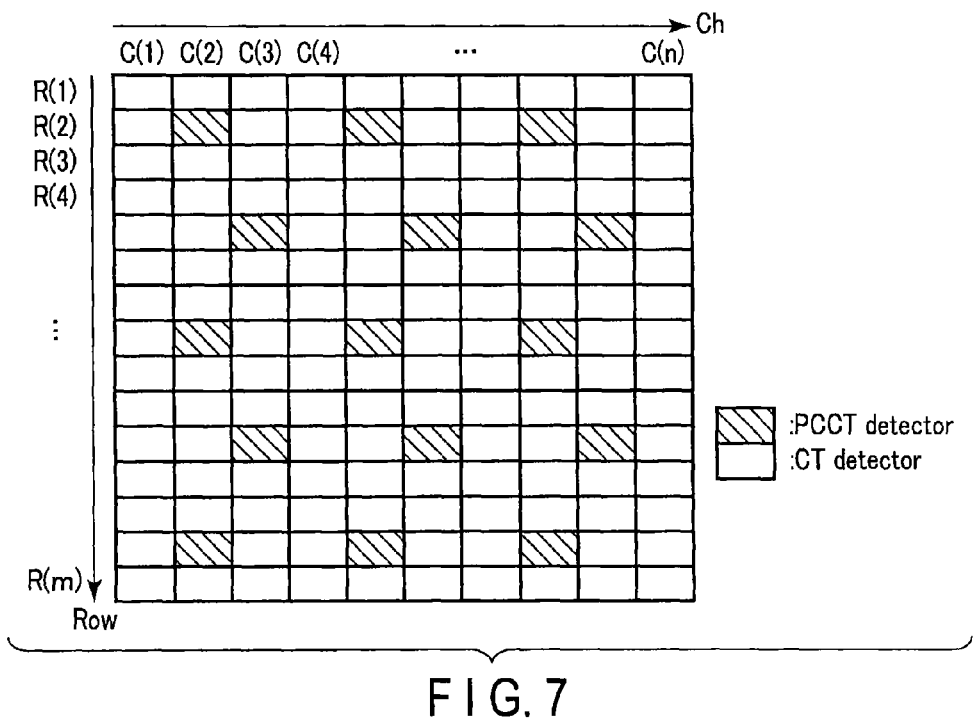
FIG. 7 is a view showing still another array pattern of the CT detectors and the PCCT detectors in FIG. 1.

In the case of the array pattern shown in FIG. 7, the plurality of CT detectors 15-1 are densely arrayed, and the plurality of PCCT detectors 15-2 are sparsely arrayed according to a predetermined rule. Therefore, the number of PCCT detectors 15-2 is much smaller than that of CT detectors 15-1, and hence it is possible to reduce the cost as compared with other array patterns.

Figure 8:
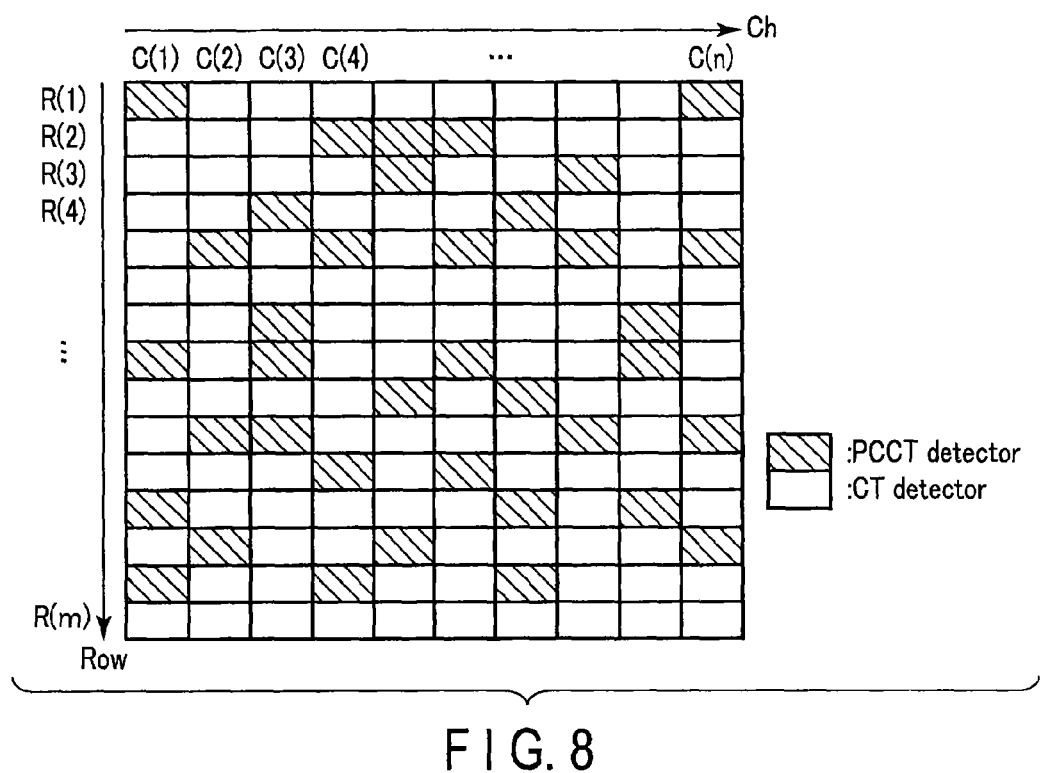
FIG. 8 is a view showing still another array pattern of the CT detectors and the PCCT detectors in FIG. 1.

In the case of the array pattern shown in FIG. 8, the plurality of CT detectors 15-1 and the plurality of PCCT detectors 15-2 are randomly arrayed. Assume that when the plurality of CT detectors 15-1 and the plurality of PCCT detectors 15-2 are regularly arrayed, an image artifact is caused by the regular array pattern. In this case, this random pattern can prevent the occurrence of this image artifact.

Figure 9:
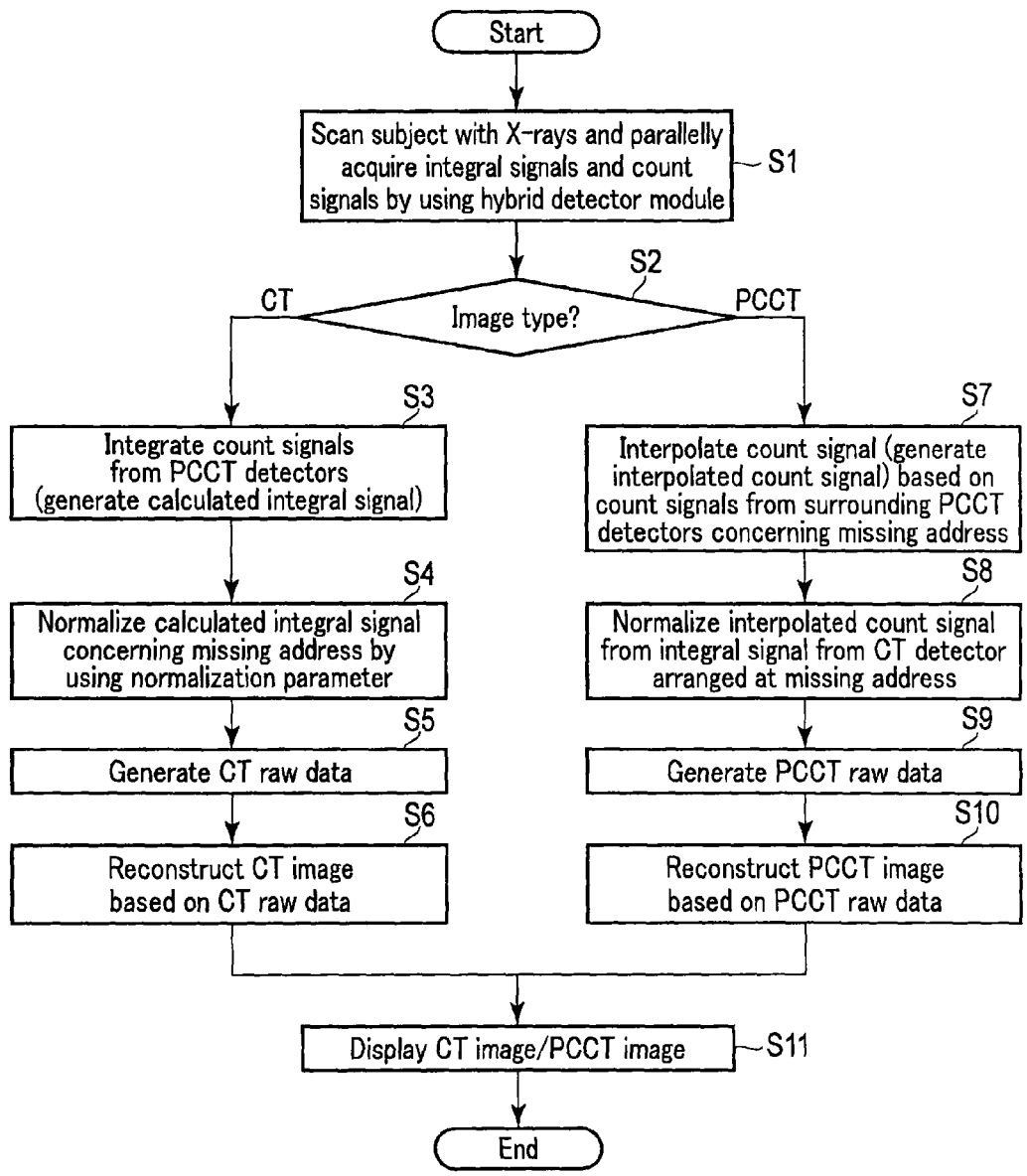
FIG. 9 is a flowchart showing a procedure for the operation of a photon counting CT apparatus according to this embodiment.

An example of the operation of the photon counting CT apparatus according to this embodiment will be described next. FIG. 9 is a flowchart showing a procedure for the operation of the photon counting CT apparatus according to the embodiment. Note that the operation example shown in FIG. 9 can be applied to either of the array patterns shown in FIGS. 4, 5, 6, 7, and 8.

As shown in FIG. 9, the system control circuitry 51 causes the imaging control circuitry 43 to execute scanning in response to an instruction to start scanning which is issued by the user via the input device 47 (step S1). In step S1, the imaging control circuitry 43 executes scanning on the subject S. Note that when executing scanning in the rest state of the top 17, i.e., executing conventional scanning, the imaging control circuitry 43 synchronously controls the hybrid detector 15, the rotation motor 19, and the high voltage generator 25. When executing scanning during the movement of the top 17, i.e., executing helical scanning, the imaging control circuitry 43 synchronously controls the hybrid detector 15, the rotation motor 19, the bed motor 23, and the high voltage generator 25. In scanning, the hybrid detector 15 simultaneously acquires an integral signal and a count signal for each of a plurality of views under the control of the imaging control circuitry 43. The signal storage 31 stores acquired integral signals and count signals.

Upon performing step S1, the system control circuitry 51 determines the image type of a reconstruction target (step S2). The user selects, as the image type of the reconstruction target, a CT image based on integral signals or a PCCT image based on count signals via the input device 47. It is possible to select an image type at any timing before, during, and end of scanning. Note that an image type may be automatically set. A case in which an image type is a CT image based on integral signals and a case in which an image type is a PCCT image based on count signals will be sequentially described below.

Figure 10:
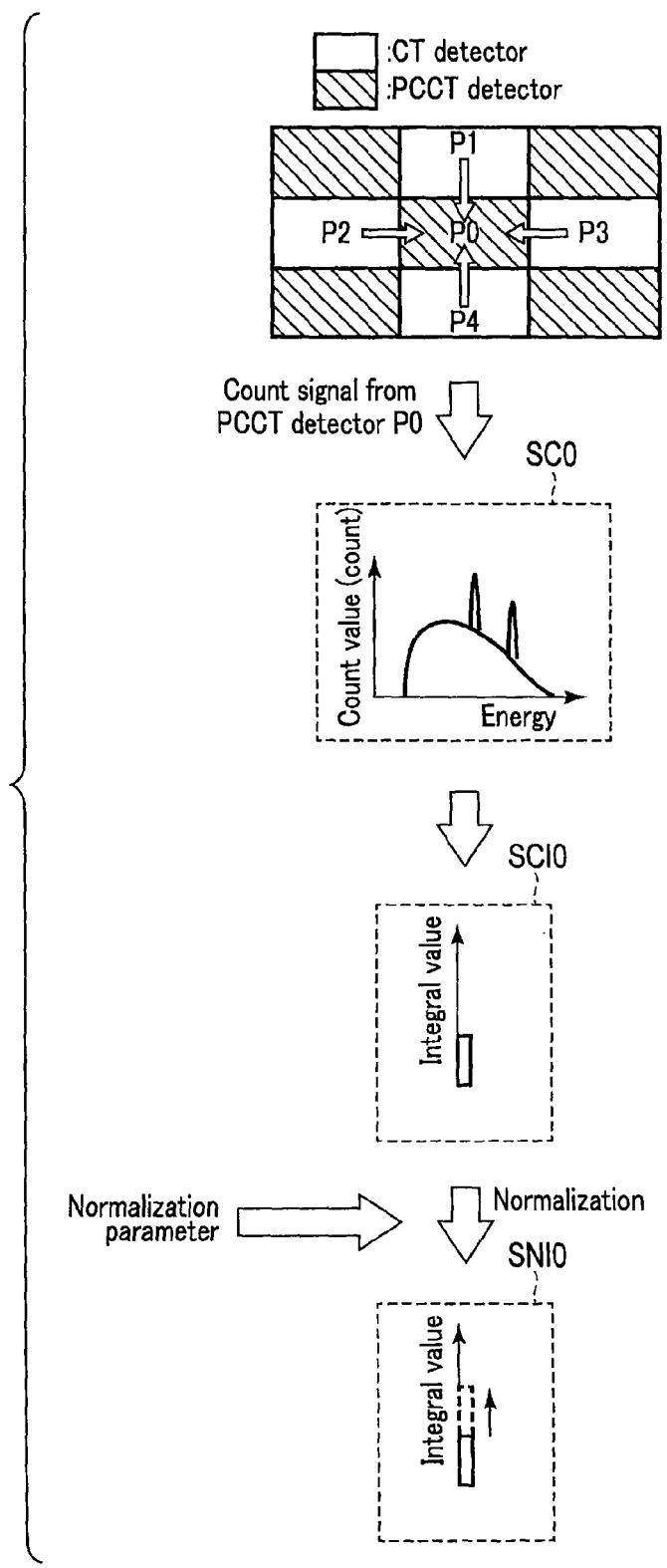
FIG. 10 is a view schematically showing a series of processing associated with the estimation of an integral signal in FIG. 9.

Upon determining that an image type is a CT image based on an integral signal (step S2: CT), the system control circuitry 51 estimates an integral signal by a series of processing in steps S3 and S4. FIG. 10 is a view schematically showing a series of processing according to the estimation of an integral signal. Referring to FIG. 10, for the sake of concreteness, assume that the plurality of CT detectors 15-1 and the plurality of PCCT detectors 15-2 are arrayed in a checkered pattern.

First of all, the system control circuitry 51 causes the integral signal generation circuitry 33 to perform generation processing (step S3). In step S3, the integral signal generation circuitry 33 generates an integral signal by integrating count signals output from the PCCT detectors 15-2. Integral signals are generated at the detector addresses of all the PCCT detectors 15-2 used for image reconstruction processing. More specifically, first of all, concerning the count signal output from the PCCT detector 15-2 arranged at a detector address P0 at which an integral signal is to be generated, the integral signal generation circuitry 33 calculates the product of an energy value in each energy band and the count value indicated by the count signal. The calculated product corresponds to the total energy of al the X-ray photons belonging to the energy band which are detected by the PCCT detector 15-2 for each view. An energy value in each energy band is set to an intermediate value, average value, or the like in the energy band. The integral signal generation circuitry 33 then calculates the integral value of a plurality of products concerning a plurality of energy bands. A digital signal indicating this integral value corresponds to an integral signal. The integral value corresponds to the total energy of all the X-ray photons detected by the PCCT detector 15-2 for each view. The generated integral signal indicates a physical amount similar to the integral signal output from the CT detector 15-1. In this manner, integral signals are generated at the detector addresses of all the PCCT detectors 15-2 used for image reconstruction processing. Each integral signal generated by the integral signal generation circuitry 33 will be referred to as a calculated integral signal hereinafter. A calculated integral signal SCI0 is calculated based on a count signal SC0 concerning the detector address (to be referred to as the missing address hereinafter) P0 at which a measured integral signal is missing.

Upon execution of step S3, the system control circuitry 51 causes the estimation circuitry 35 to perform normalization processing for a calculated integral signal (step S4). In step S4, the estimation circuitry 35 normalizes the calculated integral signal SCI0 with a normalization parameter based on the count signal SC0 output from the PCCT detector 15-2 arranged at the missing address P0. Normalization will be described in detail below.

Each CT detector 15-1 and each PCCT detector 15-2 have different detector characteristics because of structure and material differences. Detector characteristics include, for example, electrical capacitances, count rates, and detection efficiencies. Electrical capacitances are the capacitances of capacitors provided in the DASs 153-1 and 153-2 of the respective detectors 15-1 and 15-2. A count rate is defined by the count value of X-ray detection events per unit time by each of the detectors 15-1 and 15-2. In general, the CT detector 15-1 is higher in count rate than the PCCT detector 15-2. A detection efficiency is defined by the ratio of the intensity of X-rays detected by each of the detectors 15-1 and 15-2 to the intensity of incident X-rays. In general, the CT detectors 15-1 are higher in detection efficiency than the PCCT detectors 15-2. A normalization parameter is used to match the measure of the signal amount (integral value) of an interpolated integral signal SII with that of a measured integral signal SI, which differ from each other because of detector characteristic differences between the CT detector 15-1 and the PCCT detector 15-2.

The calculation of a normalization parameter by the normalization parameter calculation circuitry 41 will be described next. The normalization parameter calculation circuitry 41 calculates normalization parameters based on the integral signals acquired by the CT detectors 15-1 and the count signals acquired by the PCCT detectors 15-2 by calibration scanning. This is because all the detector characteristic differences between each CT detector 15-1 and each detector 15-2 depend on the signal amount difference between an integral signal from the CT detector 15-1 and a count signal from the PCCT detector 15-2. Calibration scanning is performed at the time of calibration before scanning performed in step S1. The imaging control circuitry 43 executes calibration scanning in response to an instruction to execute calibration scanning issued via the input device 47. A phantom having a known composition such as air or water is placed on the top 17 in calibration scanning, and X-ray CT scanning is performed on the phantom. In calibration scanning, each CT detector 15-1 detects X-rays generated from the X-ray source 13 and transmitted through the phantom and generates an integral signal concerning detected X-rays. In addition, in calibration scanning, each PCCT detector 15-2 detects the X-rays generated from the X-ray source 13 and transmitted through the phantom, and generates a count signal concerning the detected X-rays. The signal storage 31 stores the generated integral signal and count value.

Figure 11:
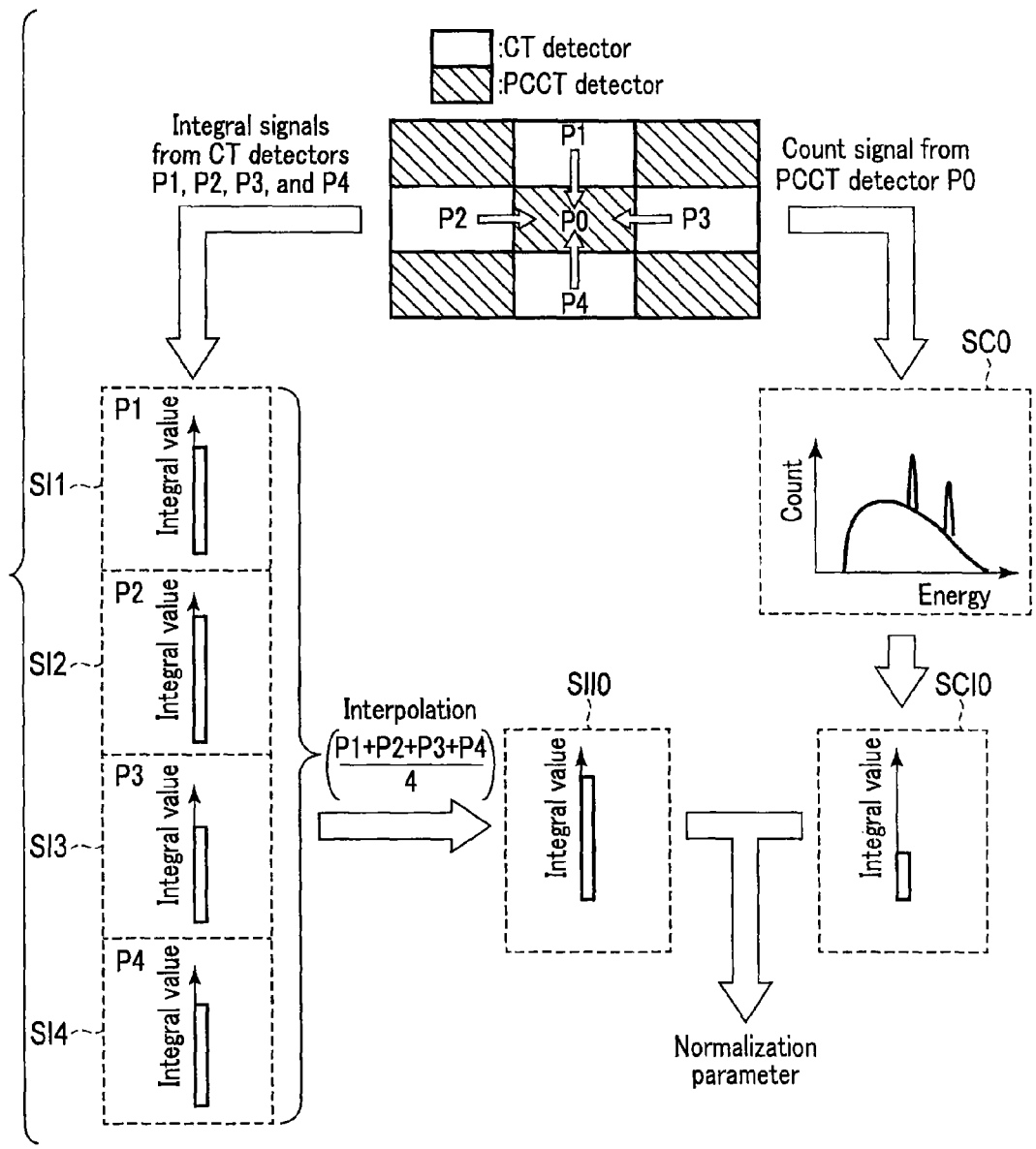
FIG. 11 is a view schematically showing a series of processing associated with the calculation of a normalization parameter by a normalization parameter calculation circuitry in FIG. 1.

FIG. 11 is a view schematically showing a series of processing concerning the calculation of a normalization parameter by the normalization parameter calculation circuitry 41. The normalization parameter calculation circuitry 41 calculates a normalization parameter for each of the plurality of PCCT detectors 15-2 based on the integral signals acquired by the CT detectors 15-1 and the count signal acquired by the PCCT detector 15-2 in calibration scanning.

For example, as shown in FIG. 11, when calculating a normalization parameter concerning the detector address P0, four detector addresses P1, P2, P3, and P4 of the CT detectors 15-1 located near the detector address P0 are set as surrounding detector addresses. When the surrounding detector addresses P1, P2, P3, and P4 are set, the normalization parameter calculation circuitry 41 obtains an interpolated integral signal SII0 concerning the detector address P0 by applying an interpolation method to integral signals at the detector addresses P1, P2, P3, and P4. As an interpolation method, there is available a nearest-neighbor method, bi-linear method, bi-cubic method, or the like used as a pixel interpolation method in image processing. When the bi-cubic method is to be used, an arbitrary interpolation function such as a Sinc function or spline function may be used. For example, as shown in FIG. 11, the interpolated integral signal SII0 concerning the detector address P0 is calculated by averaging the sum of the integral values of integral signals SI1, SI2, SI3, and SI4 concerning the four neighboring detector addresses P1, P2, P3, and P4.

Note that a method of setting surrounding detector addresses is decided in accordance with the array pattern of the CT detectors 15-1 and the PCCT detectors 15-2. For example, in the case of the array pattern shown in FIG. 4, as shown in FIG. 12, the detector addresses of the CT detectors 15-1 adjacent to the detector addresses of the PCCT detectors 15-2 are set as surrounding addresses. That is, interpolated integral signals concerning PCCT detector rows are calculated based on integral signals concerning CT detector rows. In the case of the array pattern shown in FIG. 5, interpolated integral signals concerning PCCT detector columns are calculated based on integral signals concerning CT detector columns. In the case of the array pattern shown in FIG. 7, interpolated integral signals concerning the PCCT detectors 15-2 are calculated based on integral signals concerning the CT detectors 15-1 located near the PCCT detectors 15-2. Likewise, in the case of the array pattern shown in FIG. 8, interpolated integral signals concerning the PCCT detectors 15-2 are calculated based on integral signals concerning the CT detectors 15-1 located near the PCCT detectors 15-2.

Upon calculating the interpolated signal SII0, the normalization parameter calculation circuitry 41 calculates a normalization parameter based on the signal amount of the calculated integral signal SCI0 concerning the detector address P0 and the signal amount of the interpolated integral signal SII0. More specifically, the normalization parameter calculation circuitry 41 calculates, as a normalization parameter, the ratio between the signal amount of the calculated integral signal concerning the detector address P0 and the signal amount of the interpolated integral signal SII0, more specifically, a magnification for making the signal amount of the calculated integral signal concerning the detector address P0 coincide with the signal amount concerning the interpolated integral signal SII0. With the above method, the normalization parameter calculation circuitry 41 calculates a normalization parameter for each PCCT detector 15-2. The main storage 49 stores the calculated normalization parameter for each PCCT detector 15-2.

In step S4, first of all, the estimation circuitry 35 specifies a detector address at which a measured integral signal is missing, i.e., the missing address P0. For example, the estimation circuitry 35 specifies, as a missing address, a detector address associated with a measured count signal stored in the signal storage 31. Alternatively, the estimation circuitry 35 records detector addresses associated with measured integral signals stored in the signal storage 31, and specifies, as a missing address, a detector address, of all the detector addresses, which is not recorded. Upon specifying a missing address, the estimation circuitry 35 calculates a normalized integral signal by multiplying a calculated integral signal concerning the missing address generated in step S3 by the normalization parameter associated with the missing address. The estimation circuitry 35 calculates normalized integral signals concerning all the missing addresses.

Note that a normalization parameter changes in accordance with a tube voltage. For this reason, the imaging control circuitry 43 executes calibration scanning for each of a plurality of tube voltages. It is possible to set the value of a tube voltage used for calibration scanning automatically or arbitrarily via the input device 47. The signal storage 31 stores the acquired integral signals and count signals in association with tube voltage values. The normalization parameter calculation circuitry 41 calculates a normalization parameter for each of a plurality of tube voltages.

The calculated integral signal concerning the missing address P0 is normalized by using the normalization parameter calculated by the above processing. More specifically, the estimation circuitry 35 calculates a normalized integral signal SNI0 by multiplying a calculated integral signal SCI0 concerning the missing address P0 by the normalization parameter corresponding to the tube voltage used in scanning in step S1.

Upon execution step S4, the system control circuitry 51 causes the preprocessor 37 to perform preprocessing (step S5). In step S5, the preprocessor 37 generates CT raw data concerning a plurality of views by preprocessing normalized integral signals SNI and the integral signals SI concerning the plurality of views.

Upon executing step S5, the system control circuitry 51 causes the image reconstruction circuitry 39 to perform reconstruction processing (step S6). In step S6, the image reconstruction circuitry 39 reconstructs three-dimensional CT image data based on the CT raw data generated in step S5.

According to the above description, the integral signal calculated by multiplying the calculated integral signal concerning a missing address by a normalization parameter (i.e., the normalized integral signal) is used as an integral signal concerning the missing address. However, this embodiment is not limited to this. For example, an interpolated integral signal of the measured integral signals output from the PCCT detectors 15-2 arranged at detector addresses around a missing address may be used as an integral signal concerning the missing address. This makes it possible to obtain a high-accuracy integral signal concerning a missing address without using any normalization parameter.

A procedure to be followed when an image type is a PCCT image will be described below.

Figure 13:
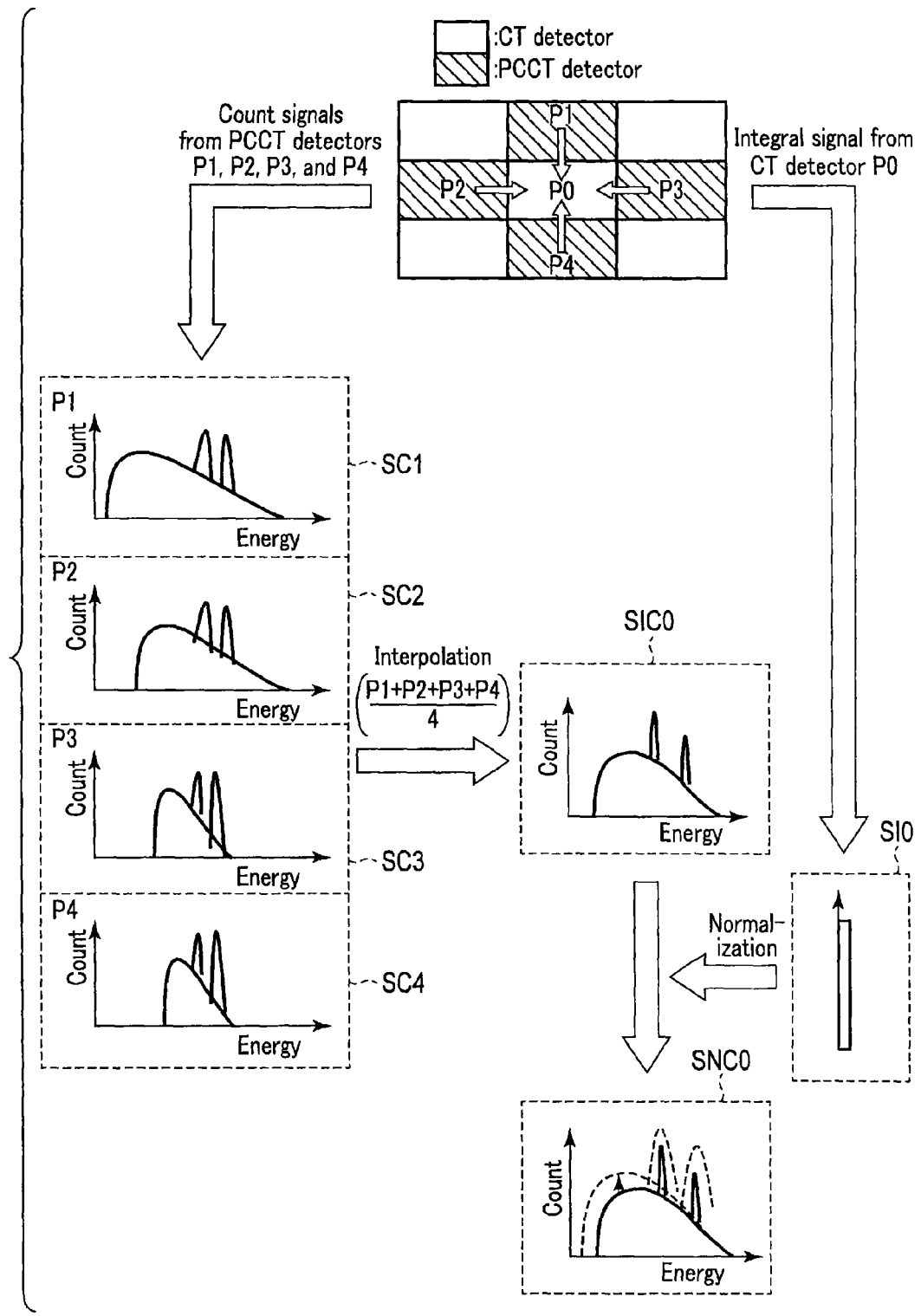
FIG. 13 is a view schematically showing a series of processing associated with the estimation of a count signal in FIG. 9.

If it is determined that an image type is a PCCT image based on a count signal (step S2: PCCT), the system control circuitry 51 estimates an integral signal by a series of processing in steps S7 and S8. FIG. 13 is a view schematically showing a series of processing concerning the estimation of a count signal. Assume that the plurality of CT detectors 15-1 and the plurality of PCCT detectors 15-2 are arrayed in a checkered pattern in FIG. 12 as in FIG. 10.

First of all, the system control circuitry 51 causes the estimation circuitry 35 to perform interpolation processing for a count signal (step S7). In step S7, the estimation circuitry 35 interpolates a count signal concerning a detector address (missing address) at which a count signal is missing, based on count signals from the PCCT detectors 15-2 arranged at detector addresses around the missing address. More specifically, as shown in FIG. 13, first of all, the estimation circuitry 35 specifies the missing address P0 concerning the CT detector 15-1. For example, the estimation circuitry 35 specifies, as a missing address, a detector address associated with an integral signal stored in the signal storage 31. Alternatively, the estimation circuitry 35 records detector addresses associated with count signals stored in the signal storage 31 and specifies, as a missing address, a detector address, of all the detector addresses, which is not recorded.

Upon specifying a missing address, the estimation circuitry 35 interpolates a count signal concerning the missing address P0 based on count signals associated with detector addresses around the missing address P0. For example, as shown in FIG. 13, when a missing address is the detector address P0 of the CT detector 15-1, the four detector addresses P1, P2, P3, and P4 of the PCCT detectors 15-2 located near the missing address P0 are set as surrounding detector addresses. A method of setting surrounding detector addresses is decided in accordance with the array pattern of the CT detectors 15-1 and the PCCT detectors 15-2. For example, in the case of the array pattern shown in FIG. 4, as shown in FIG. 12, the detector addresses of the PCCT detectors 15-2 adjacent to the detector address of the CT detector 15-1 are set as surrounding addresses. That is, count signals concerning a CT detector row are interpolated based on count signals concerning PCCT detector row. In the case of the array pattern shown in FIG. 5, count signals concerning the CT detector columns are interpolated based on count signals concerning the PCCT detector columns. In the case of the array pattern shown in FIG. 7, a count signal concerning the CT detector 15-1 is interpolated based on count signals concerning the PCCT detectors 15-2 located near the CT detector 15-1. Likewise, in the case of the array pattern shown in FIG. 8, a count signal concerning the CT detector 15-1 is interpolated based on count signals concerning the PCCT detectors 15-2 located near the CT detector 15-1.

Upon setting the surrounding detector addresses P1, P2, P3, and P4, the estimation circuitry 35 interpolates a count signal SIC0 concerning the missing address P0 by applying an interpolation method to count signals concerning the detector addresses P1, P2, P3, and P4. A count signal calculated by interpolation will be referred to as an interpolated count signal hereinafter. As an interpolation method, there is available a nearest-neighbor method, bi-linear method, bi-cubic method, or the like used as a pixel interpolation method in image processing. When the bi-cubic method is to be used, an arbitrary interpolation function such as a Sinc function or spline function may be used. For example, as shown in FIG. 13, the count value (count) of the interpolated count signal SIC0 concerning the missing address P0 is calculated by averaging the sum of the count values of count signals concerning the four neighboring detector addresses P1, P2, P3, and P4. More specifically, the estimation circuitry 35 calculates the count value of the interpolated count signal SIC0 by performing interpolation processing for the count values of the count signals SC1, SC2, SC3, and SC4 for each energy value.

Upon executing step S7, the system control circuitry 51 causes the estimation circuitry 35 to perform normalization processing for an interpolated count signal (step S8). In step S8, the estimation circuitry 35 normalizes the interpolated count signal SIC0 by using a measured integral signal SI0 from the CT detector 15-1 arranged at the missing address P0, and calculates a normalized interpolated count signal (i.e., a normalized count signal) SNC0. More specifically, the estimation circuitry 35 multiplies the integral signal SI0 by a normalization parameter, and normalizes the interpolated count signal SIC0 by using the signal amount (count value) of the integral signal SI0 multiplied by the normalization parameter, thereby the calculating a normalized count signal SNC0.

The interpolated count signal SIC0 concerning the missing address P0 is calculated based on the count signals SC1, SC2, SC3, and SC4 concerning the detector addresses P1, P2, P3, and P4 surrounding the missing address P0. That is, the interpolated count signal SIC0 does not strictly reflect the geometry of the subject S on an X-ray path reaching the CT detector 15-1 arranged at the missing address P0. In order to make the interpolated count signal SIC0 reflect the geometry of the subject S, normalization is performed based on the integral signal SI0 output from the CT detector 15-1 arranged at the missing address P0. The normalization parameter calculation circuitry 41 calculates a normalization parameter concerning each CT detector 15-1. A normalization parameter is used to match the measure of the signal amount (integral value) of the interpolated integral signal SI0 with that of the interpolated count signal SIC0, which differ from each other because of the differences in detector characteristic between the CT detector 15-1 and PCCT detector 15-2. As described above, the normalization parameter calculation circuitry 41 calculates a normalization parameter for each of the plurality of CT detectors 15-1 based on the integral signal acquired by each CT detector 15-1 and the count signal acquired by each PCCT detector 15-2 in calibration scanning executed in advance. The main storage 49 stores the calculated normalization parameter concerning each CT detector 15-1. Note that as a normalization parameter, a normalization parameter corresponding to the tube voltage used in scanning in step S1 is selected as in step S4.

Upon executing step S8, the system control circuitry 51 causes the preprocessor 37 to perform preprocessing (step S9). In step S9, the preprocessor 37 generates PCCT raw data concerning a plurality of views by preprocessing each of normalized count signals SNC and count signals SC concerning a plurality of views for each of a plurality of energy bands.

Upon executing step S9, the system control circuitry 51 causes the image reconstruction circuitry 39 to perform reconstruction processing (step S10). In step S10, the image reconstruction circuitry 39 reconstructs three-dimensional PCCT image data concerning a visualization target energy band based on the PCCT raw data generated in step S9.

Upon executing step S6 or S10, the system control circuitry 51 causes the display 45 to perform display processing (step S11). In step S11, the display 45 displays, on the display device, the CT image reconstructed in step S6 or the PCCT image reconstructed in step S10. More specifically, the display 45 displays a two-dimensional display image based on a CT image or a two-dimensional display image based on a PCCT image. A two-dimensional display image is generated by performing three-dimensional image processing for a CT image or PCCT image. As three-dimensional image processing, there are available, for example, volume rendering, surface rendering, MPR, and pixel value projection processing.

With that, the description of the operation example according to this embodiment is complete.

Note that in the above operation example, a CT image or PCCT image is reconstructed. However, this embodiment is not limited to this. That is, the system control circuitry 51 can simultaneously reconstruct a CT image and a PCCT image by simultaneously executing a series of processing in steps S3 to S7 and a series of processing in steps S8 to S11.

As described above, in the photon counting CT apparatus according to this embodiment, the hybrid detector 15 is not equipped with only the PCCT detectors 15-2, but the number of PCCT detectors 15-2 is decreased to also equip the hybrid detector 15 with the CT detectors 15-1 instead of the omitted detectors. The photon counting CT apparatus according to the embodiment can achieve reductions in the manufacturing cost and management cost of detectors as compared with a case in which the hybrid detector is equipped with only the PCCT detectors 15-2. In addition, the photon counting CT apparatus according to the embodiment can reduce the amount of data acquired by scanning as compared with the case in which the hybrid detector is equipped with only the PCCT detectors 15-2. Furthermore, when reconstructing a CT image, the photon counting CT apparatus according to the embodiment can estimate the signal amount of an integral signal concerning a missing address based on the normalization parameter based on the count signals output from the PCCT detectors 15-2 and the integral signals output from the CT detectors 15-1 in calibration scanning executed in advance, and the count signal output from the PCCT detector 15-2 arranged at the missing address in target scanning. A normalization parameter is used for the PCCT detector 15-2 arranged at each detector address to match the measure of the signal amount of a count signal concerning the detector address with that of the signal amount of an interpolated signal based on the integral signals output from the CT detectors 15-1 arranged at surrounding detector addresses. Applying the normalization parameter decided in this manner to a count signal concerning a missing address can strictly estimate the signal amount of an integral signal concerning the missing address. When reconstructing a PCCT image, the photon counting CT apparatus according to the embodiment estimates a count signal concerning a missing address based on a measured integral signal concerning the missing address and measured count signals concerning surrounding detector addresses. It is possible to more strictly estimate the signal amount of a count signal concerning a missing address by not only performing interpolation based on measured count signals concerning surrounding detector addresses in this manner but also performing normalization using a measured integral signal concerning the missing address. Having such an estimation algorithm for the signal amount of a signal concerning a missing address allows the photon counting CT apparatus according to the embodiment to reduce a deterioration in the image quality of a CT image or PCCT image caused by missing of a measured signal while including the CT detectors 15-1 and the PCCT detectors 15-2.

As has been described above, according to this embodiment, it is possible to reduce the cost of detectors and the amount of data to be acquired in photon counting CT.

In the above description, the photon counting CT apparatus belongs to the so-called third generation. That is, the photon counting CT apparatus is a rotate/rotate-type apparatus in which the X-ray source and the photon counting CT detector rotate together around the subject S. However, the photon counting CT apparatus according to this embodiment is not limited to this. For example, the photon counting CT apparatus may be a stationary/rotate-type apparatus in which many detector pixels arrayed in a ring shape are fixed, and only the X-ray source rotates around the subject S.

The words "predetermined processing circuitry" in the above description mean, for example, a dedicated or general-purpose processor, CPU, MPU, GPU, an ASIC (Application Specific Integrated Circuit), or a programmable logic device (e.g., an SPLD (Simple Programmable Logic Device), CPLD (Complex Programmable Logic Device), or FPGA (Field Programmable Gate Array)). In addition, each constituent element (each processing circuitry) of this embodiment may be implemented by a plurality of processors as well as a single processor. Furthermore, a plurality of constituent elements (a plurality of processing circuitry) may be implemented by a single processor.

The above predetermined processing circuitry may be a combination at least one of the integral signal generation circuitry 33, the estimation circuitry 35, the preprocessor 37, the image reconstruction circuitry 39, the normalization parameter calculation circuitry 41, the imaging control circuitry 43, and the system control circuitry 51.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A photon counting CT apparatus comprising:
an X-ray source configured to generate X-rays;
a hybrid detector including a plurality of integral type detectors and a plurality of photon counting type detectors, which detect X-rays generated from the X-ray source and are two dimensionally tiled on a detector array surface of the hybrid detector, the plurality of integral type detectors outputting integral signals concerning the detected X-rays, and the plurality of photon counting type detectors outputting a count signal for each of a plurality of energy bands concerning the detected X-rays; and
a processing circuitry configured to
estimate a count signal by a particular estimation target integral type detector of the plurality of integral type detectors based on an integral signal output from the particular estimation target integral type detector and a count signal output from the photon counting type detectors arranged around the particular estimation target integral type detector on the detector array surface; and
reconstruct a photon counting type image based on the estimated count signal and the count signal.

2. The apparatus of claim 1, wherein the plurality of integral type detectors and the plurality of photon counting type detectors are arranged near each other.

3. The apparatus of claim 1, wherein the estimation target integral type detector is spatially close to the one of the plurality of photon counting type detectors.

4. The apparatus of claim 3, wherein the processing circuitry interpolates the count signal concerning the estimation target integral type detector based on the count signal output from the one of the plurality of photon counting type detectors close to the estimation target integral type detector and normalizes the interpolated count signal by using the integral signal output from the estimation target integral type detector.

5. The apparatus of claim 4, wherein the processing circuitry normalizes the interpolated count signal by using the integral signal output from the estimation target integral type detector and a normalization parameter based on a calibration count signal output from the one of the plurality of photon counting type detectors and a calibration integral signal output from the estimation target integral type detector during a calibration scanning in advance of an estimation of the count signal.

6. The apparatus of claim 5, wherein the processing circuitry calculates the normalization parameter based on the calibration count signal output from the one of the plurality of photon counting type detectors and the calibration integral signal output from the estimation target integral type detector during the calibration scanning.

7. The apparatus of claim 6, wherein the calibration scanning is performed for each of a plurality of tube voltages, and
the processing circuitry calculates the normalization parameter at each of the plurality of tube voltages.

8. The apparatus of claim 1, wherein the processing circuitry
estimates an integral signal concerning an estimation target photon counting type detector of the plurality of photon counting type detectors, when a reconstruction of an integral type image is instructed, based on a normalization parameter based on a calibration count signal output from the estimation target photon counting type detector and a calibration integral signal output from one of the plurality of integral type detectors close to the estimation target photon counting type detector during a calibration scanning in advance of an estimation of the integral signal and the count signal output from the estimation target photon counting type detector.

9. The apparatus of claim 8, wherein the processing circuitry calculates the estimated integral signal by normalizing the count signal output from the estimation target photon counting type detector by using the normalization parameter.

10. The apparatus of claim 8, wherein the processing circuitry reconstructs the integral type image based on the estimated integral signal and the integral signal when the reconstruction of the integral type image is instructed.

11. The apparatus of claim 8, wherein the processing circuitry calculates the normalization parameter based on the calibration count signal output from the estimation target photon counting type detector and the calibration integral signal output from the one of the plurality of integral type detectors during the calibration scanning.

12. The apparatus of claim 11, wherein the calibration scanning is performed for each of a plurality of tube voltages, and
the processing circuitry calculates the normalization parameter at each of the plurality of tube voltages.

13. A photon counting CT apparatus comprising:
an X-ray source configured to generate X-rays;
a hybrid detector including a plurality of integral type detectors and a plurality of photon counting type detectors, which detect X-rays generated from the X-ray source and are two dimensionally tiled on a detector array surface of the hybrid detector, the plurality of photon counting type detectors outputting a count signal for each of a plurality of energy bands concerning an X-ray spectrum, and the plurality of integral type detectors outputting integral signals throughout the X-ray spectrum;

a processing circuitry configured to estimate an integral signal of a particular estimation target photon counting type detector of the plurality of photon counting type detectors based on a normalization parameter based on a calibration count signal output from the particular estimation target photon counting type detector and a calibration integral signal output from one of the plurality of integral type detectors during a calibration scanning in advance of an estimation of the integral signal, and a count signal output from the particular estimation target photon counting type detector; and reconstruct an image based on the estimated integral signal and the integral signal.

* * * * *